(12) United States Patent
Nathani et al.

(10) Patent No.: US 8,093,384 B2
(45) Date of Patent: Jan. 10, 2012

(54) PROCESSES FOR THE PREPARATION OF ALFUZOSIN

(75) Inventors: Pankaj Kumar Nathani, Dehradun (IN); Sunil Dnyaneshwar Narode, Ahmednagar (IN); Mohammad Jaweed Mukarram Siddiqui, Aurangabad (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 493 days.

(21) Appl. No.: 12/086,994

(22) PCT Filed: Dec. 14, 2006

(86) PCT No.: PCT/IB2006/003606
§ 371 (c)(1),
(2), (4) Date: Dec. 24, 2008

(87) PCT Pub. No.: WO2007/069050
PCT Pub. Date: Jun. 21, 2007

(65) Prior Publication Data
US 2009/0312351 A1    Dec. 17, 2009

(30) Foreign Application Priority Data

Dec. 16, 2005 (IN) .............................. 1585/MUM/05
Aug. 31, 2006 (IN) .............................. 1388/MUM/06

(51) Int. Cl.
*C07D 239/72* (2006.01)
(52) U.S. Cl. ...................................................... 544/291
(58) Field of Classification Search ........................ None
See application file for complete search history.

(56) References Cited

OTHER PUBLICATIONS

Manoury, et. al., Journal of Medicinal Chemistry, 1986, 29(1), 19-25.*

* cited by examiner

*Primary Examiner* — Jeffrey Murray
(74) *Attorney, Agent, or Firm* — Bio Intellectual Property Services LLC; O. (Sam) Zaghmout

(57) ABSTRACT

The invention relates to processes for the preparation of alfuzosin or pharmaceutically acceptable salts thereof in high purity. More particularly, it relates to the preparation of pure crystalline alfuzosin base. The invention also relates to pharmaceutical compositions that include the pure alfuzosin or a pharmaceutically acceptable salt thereof.

6 Claims, 3 Drawing Sheets

FIGURE 2: FTIR OF ISOLATED SOLID ALFUZOSIN BASE
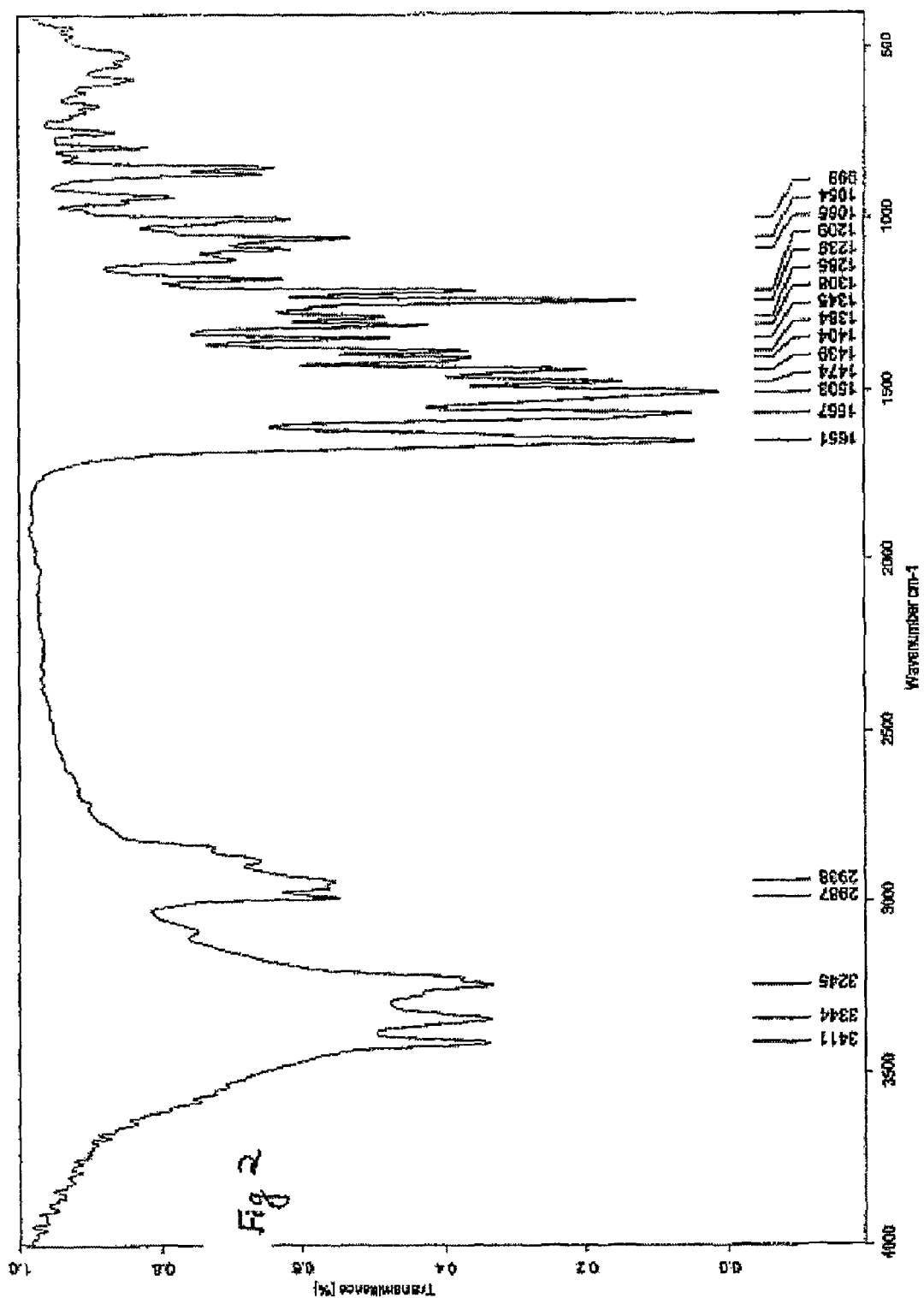

FIGURE 3: DSC OF ISOLATED SOLID ALFUZOSIN BASE
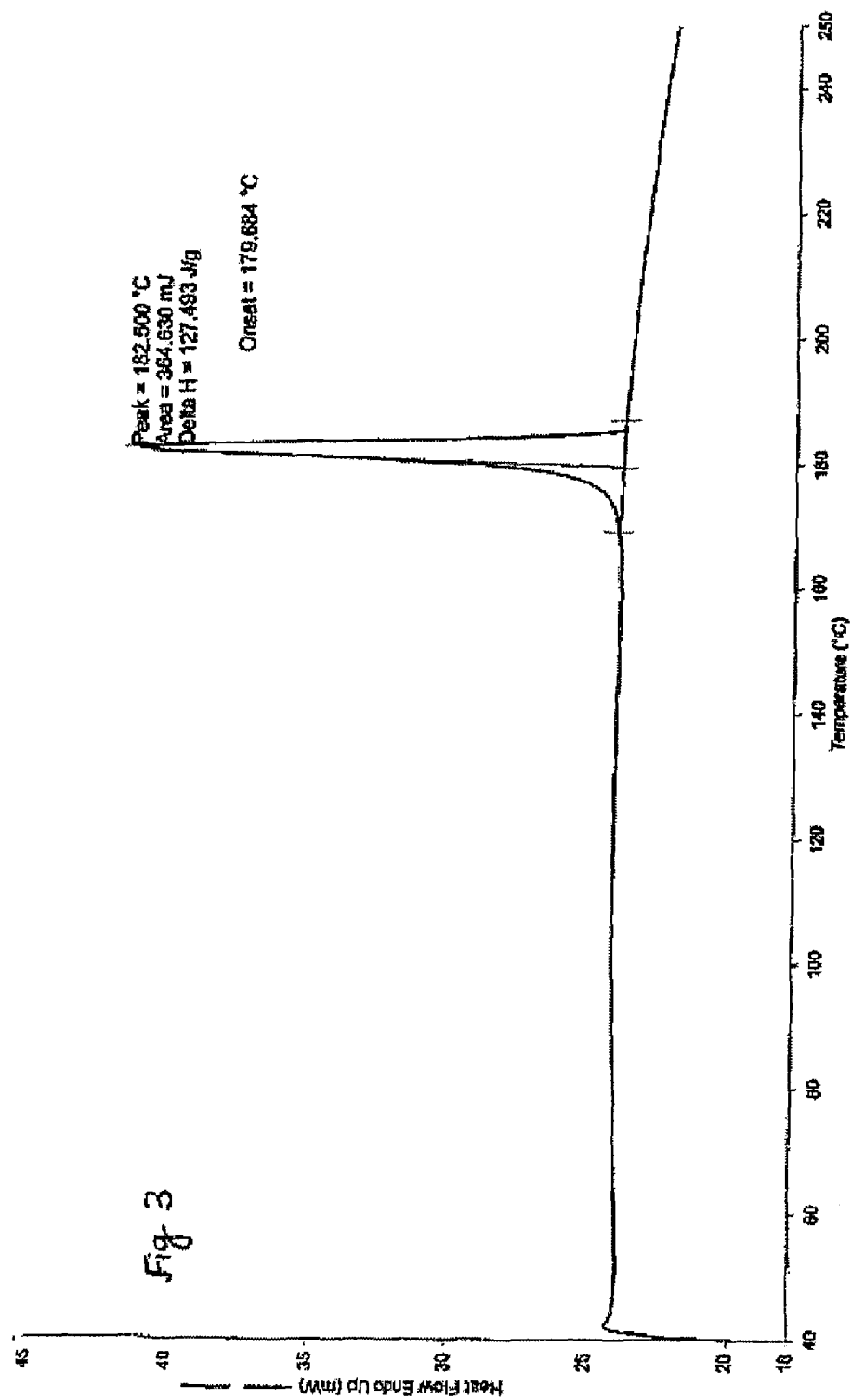

PROCESSES FOR THE PREPARATION OF ALFUZOSIN

FIELD OF THE INVENTION

The field of the invention relates to processes for the preparation of alfuzosin or pharmaceutically acceptable salts thereof in high purity. More particularly, it relates to the preparation of pure crystalline alfuzosin base. The invention also relates to pharmaceutical compositions that include the pure alfuzosin or a pharmaceutically acceptable salt thereof.

BACKGROUND OF THE INVENTION

Alfuzosin is a selective alpha$_1$-adrenergic blocker indicated for the treatment of benign prostatic hyperplasia (BPH). Chemically, alfuzosin is N-[3-[(4-Amino-6,7-dimethoxy-2-quinazolinyl)methylamino]propyl]tetrahydro-2-furan carboxamide. It is commercially available in the form of its hydrochloride salt of structural Formula I for the treatment of the symptoms associated with benign prostatic hyperplasia. Alfuzosin is indicated for the treatment of moderate to severe symptoms of benign prostatic hyperplasia.

FORMULA I

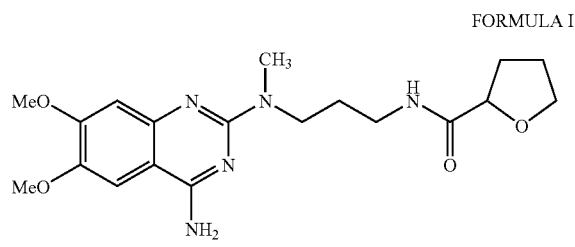

U.S. Pat. No. 4,315,007 and *Journal of Medicinal Chemistry* 1986, 29, 19-25 provides processes for the preparation of alfuzosin. In general, the processes either involve high vacuum distillation of intermediates or a high-pressure hydrogenation of the nitrile intermediate. The anhydrous product obtained by following these processes is highly hygroscopic and is usually contaminated with amorphous form. In addition, the product obtained is not adequately pure for incorporation in to the pharmaceutical dosage forms.

GB 2231571 provides another process for the preparation of alfuzosin, which also involves intermediates that require high vacuum distillations. The disclosed method also uses corrosive chemicals such as phosphorous trichloride and phosphorous oxychloride. The yields obtained as per this process are lower and the product purity is not disclosed.

U.S. Pat. No 5,545,738 provides processes for the preparation of alfuzosin hydrochloride dihydrate from the anhydrous alfuzosin hydrochloride.

SUMMARY OF THE INVENTION

The present inventors have developed a novel process for preparation of alfuzosin or salts thereof in high purity. The process does not involve high vacuum distillation to isolate and purify the intermediates. Further, the present inventors have found that the hydrogenation of the nitrile intermediate can be carried out at a much lower hydrogen pressure than that reported in the known art by changing the reaction conditions. The present inventors have also isolated alfuzosin base in solid form. The solid alfuzosin base can further be purified and can also be converted to its salt having purity more than 99% when measured by HPLC.

The present inventors also have developed a process for purification of alfuzosin hydrochloride through methanol solvate formation. It was found that alfuzosin hydrochloride obtained by this method has purity of 99% or above when measured by HPLC.

The details of one or more embodiments of the inventions are set forth in the description below. Other features, objects and advantages of the inventions will be apparent from the description and claims.

DESCRIPTION OF THE DRAWINGS

FIG. 2 is a Fourier Transform Infrared (FTIR) spectrum of alfuzosin base.
FIG. 3 is a Differential Scanning Calorimetric (DSC) thermogram of alfuzosin base.

DETAILED DESCRIPTION OF THE INVENTION

Figure 1:
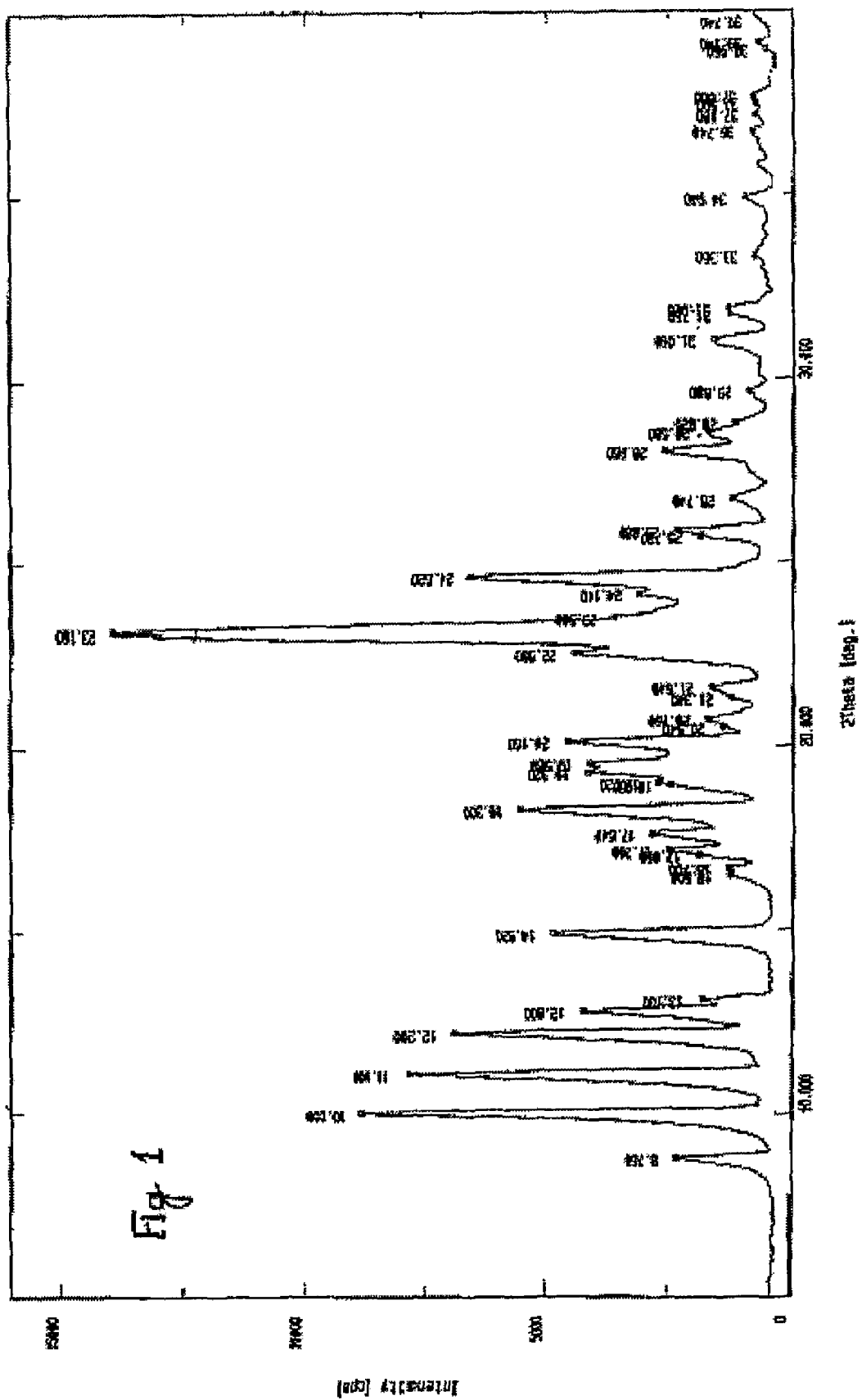
FIG. 1 is an X-Ray Diffraction Pattern of alfuzosin base.

A first aspect of the present invention provides a process for the preparation of alfuzosin of Formula I or salts thereof.

FORMULA I

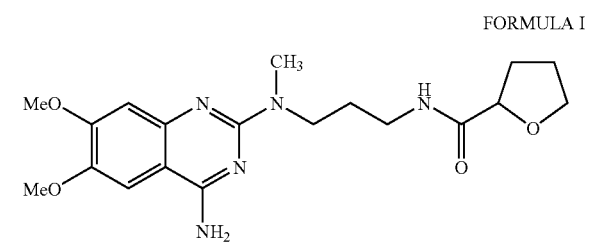

The process includes the steps of:
a) reacting an amine of Formula II or a salt thereof,

FORMULA II

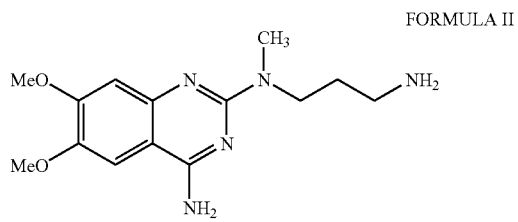

with a mixed anhydride of tetrahydro-2-furoic acid of Formula III,

FORMULA III

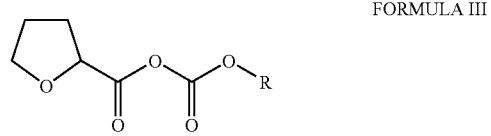

wherein R is alkyl, aryl, aralkyl or an ester residue, in the presence of a proton acceptor; and
b) isolating the alfuzosin or a salt thereof from the reaction mass thereof.

A second aspect of the present invention provides a process for the preparation of alfuzosin of Formula I or salts thereof.

The process includes the steps of:
a) hydrogenating a nitrile of Formula V,

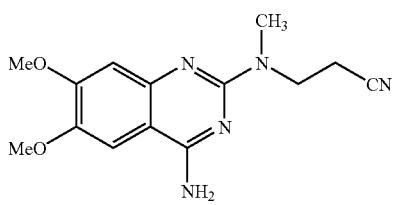

FORMULA V in the presence of Raney nickel and a primary alcohol using a base to get amine of Formula II;

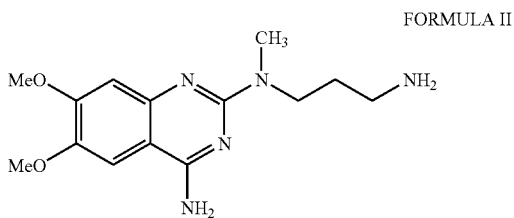

FORMULA II b) reacting the amine of Formula II or a salt thereof with a mixed anhydride of tetrahydro-2-furoic acid of Formula III in the presence of a proton acceptor; and

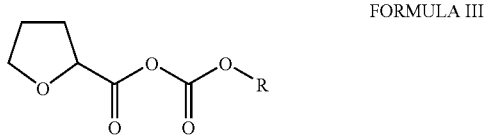

FORMULA III c) isolating the alfuzosin or a salt thereof from the reaction mass thereof.

A third aspect of the present invention provides a process for the preparation of nitrile of Formula V.

The process includes the steps of:
a) reacting aminoquinazoline of Formula VI with 3-(methylamino)propionitrile in the presence of a polar aprotic solvent; and

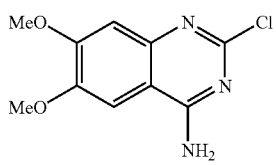

FORMULA VI b) isolating the nitrile of Formula V from the reaction mass thereof.

A fourth aspect of the present invention provides a crystalline solid alfuzosin base of Formula I.

A fifth aspect of the present invention provides crystalline solid alfuzosin base having characteristic X-ray diffraction pattern as depicted in FIG. 1.

A sixth aspect of the present invention provides crystalline solid alfuzosin base having characteristic infra-red spectrum as depicted in FIG. 2.

A seventh aspect of the present invention provides crystalline solid alfuzosin base having characteristic differential scanning calorimetry (DSC) meting exotherm obtained at about 178-185° C. The DSC thermogram of crystalline alfuzosin base is provided as FIG. 3.

An eighth aspect of the present invention provides a pharmaceutical composition comprising crystalline alfuzosin base; and one or more pharmaceutically acceptable carriers, excipients or diluents.

A ninth aspect of the present invention provides a process for the preparation of acid addition salts of alfuzosin, the process comprising reacting crystalline alfuzosin base with an acid.

A tenth aspect of the present invention provides anhydrous alfuzosin hydrochloride having purity more than 99% by HPLC.

An eleventh aspect of the present invention provides anhydrous alfuzosin hydrochloride having purity more than 99.5%.

A twelfth aspect of the present invention provides anhydrous alfuzosin hydrochloride having purity more than 99.9%.

Aminoquinazoline of Formula VI can be prepared by any method known in the art and can be used as starting material for the present invention. It is reacted with 3-(methylamino) propionitrile in the presence of a polar aprotic solvent at a temperature of from about 110° C. to about 150° C. The solvent choice is decided by the fact that it assists the reaction completion and at the same time has no solubility for the product. Examples of such solvents include N,N-dimethylacetamide, N,N-dimethylformamide, dimethylsulphoxide, acetonitrile, and N-methylpyrrolidone. After completion of the reaction, the mass is cooled and the product, the nitrile of Formula V is filtered from the reaction mass without further work-up or any high vacuum distillation.

The nitrile of Formula V is subjected to the hydrogenation reaction in the presence of an alcohol as solvent and Raney Nickel as catalyst using a base. The base can be selected from alkali metal or alkaline earth metal hydroxide, hydride, alkoxide and ammonia. Examples of bases include sodium hydroxide, potassium hydroxide, calcium hydroxide, sodium or potassium hydride, sodium or potassium methoxide, ethoxide, isopropoxide or tert-butoxide. The hydrogenation reaction can be carried out at a hydrogen pressure of about 175-300 pound per square inch (PSI). The temperature of the reaction can be maintained from about 25° C. to about the reflux temperature of the alcohol used. The alcohol can be selected from methanol, ethanol, n-propanol, isopropanol or mixtures thereof After completion of the hydrogenation, the pressure is released and the catalyst is filtered. The filtrate is concentrated and the residue is treated with aqueous alkali solution and stirred to get slurry. The solid separated is filtered and washed with water and dried to get the desired amine of Formula II. No further processing is required for the purification purpose and the so obtained product can be used as such for the next reactions.

Tetrahydro-2-Furoic acid of Formula IIIA is converted to its mixed anhydride by reacting with a compound of Formula IV, wherein R is substituted or un-substituted $C_{1-6}$alkyl, aryl, aralkyl or a suitable ester residue and X is a halogen, in the presence of a suitable organic solvent and a base.

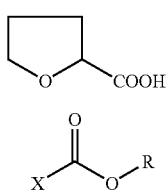

Formula IIIA

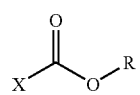

Formula IV

Examples of the compound of Formula IV include methyl chloroformate, ethyl chloroformate, phenyl chloroformate or benzyl chloroformate. The organic solvent can be selected from aromatic hydrocarbon, halogenated hydrocarbon, non-polar aprotic solvent or mixtures thereof. The base can be selected from amine, alkoxide or the like. To the so obtained mixed anhydride of 2-furoic acid of Formula III is added $N_1$-(4-amino-6,7-dimethoxyquinazol-2yl)-$N_1$-methylpropyldiamine of Formula II under controlled rate of addition and the resultant mass is further stirred for about 1-4 hours in presence of proton acceptor. The proton acceptor is selected from a group comprising of alkali or alkaline earth metal hydroxides, alkoxides, carbonates, bicarbonates; primary or secondary or tertiary amines or the like. After completion of the reaction, the reaction mass is basified, mixed with water and the organic layer is separated, washed with water and finally concentrated under reduced pressure. The residue is mixed with methanol and stirred to form slurry, which is filtered to get alfuzosin base in solid form.

The so obtained base can be purified in several ways. It can be slurry washed with a suitable solvent or can be recrystallized from a suitable organic solvent to remove the impurities. It can also be treated with activated charcoal to remove coloring impurities. The suitable organic solvent comprises one or more of $C_{1-4}$ alkanol, polar aprotic solvent, aromatic hydrocarbon or mixtures thereof. The isolated, solid alfuzosin base may be characterized by X-ray diffraction pattern, infrared spectra and Differential Scanning Calorimetric as depicted in FIGS. 1, 2 and 3, respectively.

The isolated, solid alfuzosin base so obtained can be converted to its acid addition salt by dissolving it in a suitable organic solvent and treating it with an acid. For example, in order to obtain hydrochloride salt of alfuzosin, the solution of isolated solid alfuzosin base in $C_{1-4}$ alkanol is reacted with hydrogen chloride. The mixture can be heated to reflux followed by the addition of a suitable anti-solvent at elevated temperature. The anti-solvent is characterized by the fact that the acid addition salt of alfuzosin is insoluble, practically insoluble or very slightly soluble in the anti-solvent. The terms insoluble, practically insoluble or very slightly soluble have their ordinary meanings as defined in United States Phamacopoeia 2002. The resultant mass can be gradually cooled to about 0-35° C. and filtered to get the anhydrous alfuzosin hydrochloride having purity greater than 99% by HPLC.

A thirteenth aspect of the present invention provides a process for the preparation of alfuzosin hydrochloride. The process includes the steps of:
 a) treating alfuzosin base with alcoholic hydrogen chloride to get alfuzosin hydrochloride alcohol solvate;
 b) isolating the alcohol solvate of alfuzosin hydrochloride;
 c) refluxing the alcohol solvate with acetone; and
 d) isolating the alfuzosin hydrochloride from the reaction mass thereof.

Alfuzosin base used as starting material can be prepared by methods known in the art. It is then suspended in an alcoholic solvent and treated with alcoholic hydrogen chloride. The suitable alcohol may be selected from a group comprising one or more of $C_1$-$C_4$ linear chain or branched chain alcohols. Examples of alcohols include methanol, ethanol, n-propanol, isopropanol, butanol and isobutanol. The alcohol solvate of alfuzosin hydrochloride is isolated from the reaction mass and refluxed with acetone to free the solvated alcohol. The so obtained alfuzosin hydrochloride has purity of 99% or above.

The present invention is further illustrated by the following examples which are provided merely to be exemplary of the invention and do not limit the scope of the invention. Certain modifications and equivalents will be apparent to those skilled in the art and are intended to be included within the scope of the present invention.

Example-1

N-4-amino-6,7-dimethoxyquinazol-2-yl)-N-methyl-2-cyanoethylamine (II)

A mixture of 4-Amino-2-chloro-6,7-dimethoxyquinazoline (500 gm) and 3-(methylamino)propionitzile (265 gm) in N,N-dimethylacetamide (1.0 L) was heated at 125 to 135° C. for two hours. The reaction mixture was cooled to ambient temperature and the separated solid was filtered. The wet solid so obtained was washed with N,N-dimethylacetamide and dried to get the title compound.
Yield: 465 gm Example-2

$N_1$-(4-Amino-6,7-methoxyquinazol-2-yl)-$N_1$-methylpropylenediamine (III)

A mixture of N-(4-Amino-6,7-methoxyquinazol-2-yl)-N-methyl-2-cyanoethylamine (450 gm) in methanolic sodium hydroxide solution (152 gm sodium hydroxide dissolved in 4.0 L methanol) was hydrogenated under 200 PSI of hydrogen pressure at 70 to 80° C. in presence of Raney Nickel for 2 to 3 hours. After the completion of the reaction, the catalyst was filtered and the filtrate was concentrated to get a residue. The residue obtained was stirred with dilute sodium hydroxide solution for three hours. The resulting slurry was filtered and the solid obtained was washed with water and dried under vacuum to get the title compound.
Yield: 373 gm Example-3

N-[3-[(4-Amino-6,7-dimethoxy-2-quinazolinyl)methylamino)propyl]tetrahydro-2-furan Carboxamide (Alfuzosin)

To a mixture of terahydrofuroic-2-acid (99.7 gm) and dichloromethane (600ml) at 0 to 5° C., triethylamine (86.8 gm) was added. To the resulting reaction mixture, ethyl chloroformate (93.2 gm) was added at low temperature. The reaction mixture was further stirred for one hour and a slurry of $N_1$-(4-Amino-6,7-dimethoxyquinazol-2-yl)-$N_1$-methylpropylenediamine (100 gm) in dichloromethane (400 ml) was added. The resultant mixture was stirred for about one hour for the completion of the reaction and sodium hydroxide solution (500 ml, 1N) was added. The layers were separated and the organic layer was washed with sodium hydroxide solution and concentrated under vacuum. The residue thus obtained was stirred with methanol (200 ml) for three hours to get slurry, which was filtered to get alfuzosin base in solid form. The product thus obtained was re-crystallized from methanol to get pure, isolated, solid alfuzosin base.
Yield: 75 gm
Purity: 99.8%

Example-4

N-[3-[(4-Amino-6,7-dimethoxy-2-quinazolinyOm-ethylamino]propylitetrahydro-2-furan carboxamide hydrochloride (Alfuzosin hydrochloride)

To a mixture of terahydrofuroic-2-acid (99.7 gm) and dichloromethane (600ml) at 0 to 5oC, triethylamine (86.8 gm) was added. To the resulting reaction mixture, ethyl chloroformate (93.2 gm) was added at low temperature. The reaction mixture was further stirred for one hour and a slurry of N1-(4-Amino-6,7-dimethoxyquinazol-2-yl)-N1-methylpropylenediamine (100 gm) in dichloromethane (400 ml) was added. The resultant mixture was stirred for about one hour for the completion of the reaction and sodium hydroxide solution (500 ml, 1N) was added. The layers were separated and the organic layer was washed with sodium hydroxide solution and concentrated under vacuum to get syrupy mass. The syrupy mass thus obtained is dissolved methanol (240 ml) and the pH of the suspension was adjusted between 4 to 6 using methanolic hydrochloric acid. The reaction mixture was further stirred at room temperature for 4 hours and filtered. The wet solid was refluxed with acetone for 2 hours then cooled to room temperature. The product is isolated and dried to get the anhydrous alfuzosin hydrochloride.
Yield: 76 gm
HPLC purity: 99.10% by HPLC

Example-5

N-[3-[ (4-Amino-6,7-dimethoxy-2-quinazolinyl) methylamino]propyl]tetrahydro-2-furan carboxamide hydrochloride (Alfuzosin hydrochloride)

To a suspension of N-[3-[(4-Amino-6,7-dimethoxy-2-quinazolinyl)methyl amino]propyl] tetahydro-2-furan carboxamide (70 gm) in methanol (350 ml) methanolic hydrogen chloride solution was added. The resulting reaction mixture was heated to about 60° C. and isopropyl ether (700 ml) was added to it. The resultant mass was gradually cooled to room temperature and the separated solid was collected by filtration to get the hydrochloride salt of alfuzosin in anhydrous form.
Yield: 70 gm
Purity: 99.9%

Example-6

Preparation of Alfuzosin hydrochloride methanol solvate

Alfuzosin base N-[3-[(4-Amino-6,7-dimethoxy-2-quinazoliny pmethylam ino] propyl] tetahydro-2-furan carboxamide (73 gm) was suspended in methanol (240 ml) and the pH of the suspension was adjusted between 4 to 6 using methanolic hydrochloric acid. The reaction mixture was further stirred at room temperature for 4 hours and filtered. The wet solid was dried to get the alfuzosin hydrochloride methanol solvate.
Yield: 82 gm
HPLC purity: 99.13% by HPLC While the present invention has been described in terms of its specific embodiments, certain modifications and equivalents will be apparent to those skilled in the art and are intended to be included within the scope of the present invention.

We claim:

1. A process for the preparation of alfuzosin of Formula I or a salt thereof,

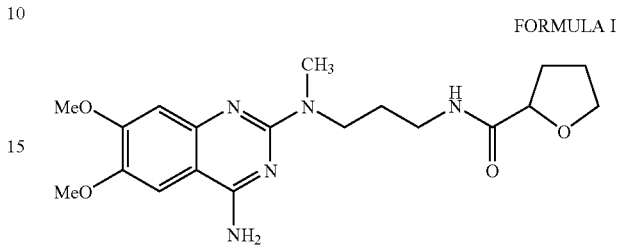

FORMULA I the process comprising:
a) reacting an amine of Formula II or a salt thereof,

FORMULA II with a mixed anhydride of tetrahydro-2-furoic acid of Formula III,

FORMULA III wherein R is alkyl, aryl, aralkyl or an ester residue, in the presence of a proton acceptor; and
b) isolating the alfuzosin or a salt thereof from the reaction mass thereof.

2. The process of claim 1, wherein the mixed anhydride of tetrahydro-2-furoic acid is prepared by reacting tetrahydro-2-furoic acid with methyl chloroformate, ethyl chloroformate, phenyl chloroformate or benzyl chloroformate.

3. A process for the preparation of alfuzosin of Formula I or a salt thereof,

FORMULA V the process comprising:
 a) hydrogenating a nitrile of Formula V,

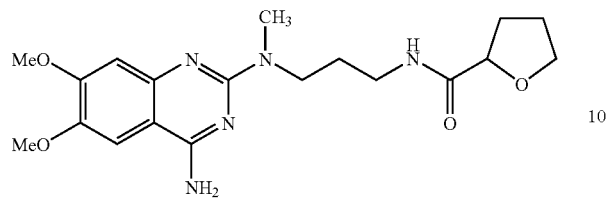

FORMULA I in the presence of Raney nickel and a primary alcohol using a base to get amine of Formula II;

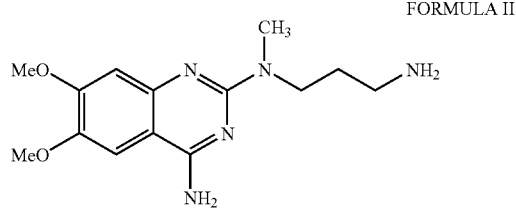

FORMULA II b) reacting the amine of Formula II or a salt thereof with a mixed anhydride of tetrahydro-2-furoic acid of Formula III in the presence of a proton acceptor; and

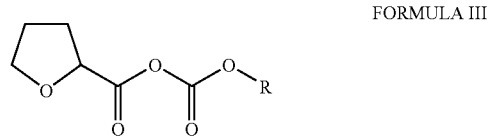

FORMULA III wherein R is alkyl, aryl, aralkyl or an ester residue, in the presence of a proton acceptor; and c) isolating the alfuzosin or a salt thereof from the reaction mass thereof.

4. The process of claim 3, wherein the hydrogenation is carried out at a hydrogen pressure of about 175-300 pound per square inch (PSI).

5. The process of claim 3, wherein the base comprises one or more of hydroxides, alkoxides, and hydrides of alkali and alkaline earth metals, and ammonia.

6. The process of claim 3, wherein the primary alcohol comprises one or more of methanol, ethanol, n-propanol and isopropanol.

* * * * *